United States Patent
Ponder et al.

(10) Patent No.: US 9,540,289 B2
(45) Date of Patent: Jan. 10, 2017

(54) CHELATED COMPOSITIONS AND METHODS OF MAKING AND USING THE SAME

(71) Applicant: Scott G. Williams, LLC, Conyers, GA (US)

(72) Inventors: Sherman M. Ponder, Conyers, GA (US); Fernando Remigio Munoz, Atlanta, GA (US)

(73) Assignee: Scott G. Williams, LLC, Conyers, GA (US)

( * ) Notice: Subject to any disclaimer, the term of this patent is extended or adjusted under 35 U.S.C. 154(b) by 0 days.

(21) Appl. No.: 14/714,983

(22) Filed: May 18, 2015

(65) Prior Publication Data

US 2015/0299059 A1  Oct. 22, 2015

Related U.S. Application Data

(63) Continuation of application No. 14/195,560, filed on Mar. 3, 2014, now Pat. No. 9,034,071, which is a
(Continued)

(51) Int. Cl.
*A23L 29/00* (2016.01)
*C05D 9/02* (2006.01)
(Continued)

(52) U.S. Cl.
CPC .............. *C05D 9/02* (2013.01); *A23L 29/015* (2016.08); *C05D 3/00* (2013.01); *C05G 3/0029* (2013.01); *C05G 3/0035* (2013.01); *C05G 3/0041* (2013.01); *C07F 3/003* (2013.01); *C07F 3/06* (2013.01); *C07F 15/025* (2013.01)

(58) Field of Classification Search
CPC ........................................................ C05D 9/02
See application file for complete search history.

(56) References Cited

U.S. PATENT DOCUMENTS 2,860,448 A  11/1958  Carasso et al.
2,931,716 A   4/1960  Kelley et al.
(Continued)

FOREIGN PATENT DOCUMENTS

WO  2012/088138 A1  6/2012

OTHER PUBLICATIONS

International Search Report and Written Opinion for PCT Patent Application Serial No. PCT/US20111066213, mailed on Apr. 23, 2012, 8 pages.
(Continued)

*Primary Examiner* — Wayne Langel
(74) *Attorney, Agent, or Firm* — Brake Hughes Bellermann LLP

(57) ABSTRACT

A composition includes a first chelating agent, a second chelating agent, and a plurality of metal ions. In one embodiment, the second chelating agent includes citric acid and is different than the first chelating agent. A method for forming a composition includes mixing a first chelating agent, a second chelating agent, and a metal salt together to form a mixture and processing the mixture to form at least one of a granulated composition and a powdered composition. In some embodiments, the second chelating agent includes citric acid and is different than the first chelating agent.

12 Claims, 1 Drawing Sheet

Related U.S. Application Data continuation of application No. 12/976,627, filed on Dec. 22, 2010, now Pat. No. 8,685,133.

(51) Int. Cl.
*C05G 3/00* (2006.01)
*C07F 3/00* (2006.01)
*C07F 3/06* (2006.01)
*C07F 15/02* (2006.01)
*C05D 3/00* (2006.01)

(56) References Cited

U.S. PATENT DOCUMENTS

| | | | |
|---|---|---|---|
| 2,961,311 A | 11/1960 | Bersworth et al. | |
| 3,038,793 A | 6/1962 | Kroll et al. | |
| 3,051,563 A | 8/1962 | Bersworth et al. | |
| 3,130,038 A | 4/1964 | Thomas et al. | |
| 3,423,199 A | 1/1969 | Philen et al. | |
| 3,492,238 A | 1/1970 | Wohlberg et al. | |
| 3,520,651 A | 7/1970 | Philen et al. | |
| 3,523,019 A | 8/1970 | Philen et al. | |
| 3,961,932 A | 6/1976 | Miller | |
| 4,219,349 A | 8/1980 | Bardsley | |
| 4,332,609 A | 6/1982 | Ott | |
| 4,505,732 A * | 3/1985 | Aigner | C05D 9/02 71/11 |
| 4,786,307 A | 11/1988 | Marihart | |
| 5,019,149 A | 5/1991 | Hawkins et al. | |
| 5,274,151 A | 12/1993 | Thunberg | |
| 5,366,533 A | 11/1994 | Behel, Jr. | |
| 5,372,626 A | 12/1994 | Zivion et al. | |
| 5,446,179 A | 8/1995 | Thunberg | |
| 5,504,055 A | 4/1996 | Hsu | |
| 5,772,723 A | 6/1998 | Robinett et al. | |
| 5,917,111 A | 6/1999 | Robinett et al. | |
| 5,997,600 A | 12/1999 | Dean | |
| 6,080,220 A | 6/2000 | Sequi et al. | |
| 6,248,842 B1 | 6/2001 | Singh et al. | |
| 6,383,245 B1 | 5/2002 | Yamashita | |
| 6,383,247 B1 | 5/2002 | Wiechens | |
| 6,429,225 B1 | 8/2002 | Nagai et al. | |
| 6,689,392 B2 | 2/2004 | Lifshitz | |
| 6,746,660 B1 | 6/2004 | Chiang et al. | |
| 6,858,058 B2 | 2/2005 | Daniels | |
| 6,870,026 B1 | 3/2005 | Dean | |
| 8,685,133 B2 * | 4/2014 | Ponder | C05D 9/02 71/27 |
| 2003/0101785 A1 | 6/2003 | Jia et al. | |
| 2009/0078014 A1 | 3/2009 | Yamashita | |
| 2010/0158806 A1 | 6/2010 | Bolotin et al. | |
| 2012/0103041 A1 * | 5/2012 | Smith | C05B 17/00 71/27 |
| 2012/0160001 A1 | 6/2012 | Ponder et al. | |
| 2013/0247630 A1 | 9/2013 | Reichwein et al. | |

OTHER PUBLICATIONS

International Preliminary Report on Patentability for International Application No. PCT1US2011/066213, mailed on Jul. 4, 2013, 7 pages.

Brandt Consolidated, Inc., "Brandt Citric Copper—A Citrate Chelate for Prevention and Correction of Copper Deficiencies", Specimen Label, 1 page.

Brandt Consolidated, Inc., "Brandt Citric Manganese—A Citrate Chelate for Prevention and Correction of Manganese Deficiencies", Specimen Label, 1 page.

Brandt Consolidated, Inc., "Brandt Citric Zinc—A Citrate Chelate for Prevention and Correction of Zinc Deficiencies", Specimen Label, 1 page.

Chemical Dynamics, Inc., "Safety-Iron+Stain-Less Formulation", Specimen Label, Revised Jan. 17, 2006, 1 page.

CNI Agriminerals, "Chem-Starter(TM) Liquid Zinc", Specimen Label, 2006, 1 page.

CNI Agriminerals, "Chem-Starter(TM) Pop-Up for Corn", Specimen Label, 2006, 1 page.

Chemical Dynamics, Inc., "Dynazyme®", Chelated Essential Micronutrients", Specimen Label, Rev. Aug. 18, 2005, 1 page.

Chemical Dynamics, Inc., "Dyna Green(TM) Potato Mix", Manufactured by Chemical Dynamics, Inc., Rev. Mar. 5, 2007, Specimen Label, 1 page.

Douglass Fertilizer & Chemical, "Citrus Power", SunGlo Nutritionals, Specimen Label, 1 page.

Douglass Fertilizer & Chemical, "SunGlo Iron +2Mn", SunGlo Nutritionals, Specimen Label, 1 page.

Douglass Fertilizer & Chemical, "SunGlo MZF", SunGlo Nutritionals, Specimen Label, 1 page.

Douglass Fertilizer & Chemical, "Vegetable Power", SunGlo Nutritionals, Specimen Label, 1 page.

Helena Holding Company, "TraFix® ZM", 2007, Specimen Label, 1 page.

Helena Holding Company, "TraFix® Zn", 2006, Specimen Label, 1 page.

Helena Holding Company, "Tracite® LF Row Crop Mix", 2007, Specimen Label, 1 page.

* cited by examiner

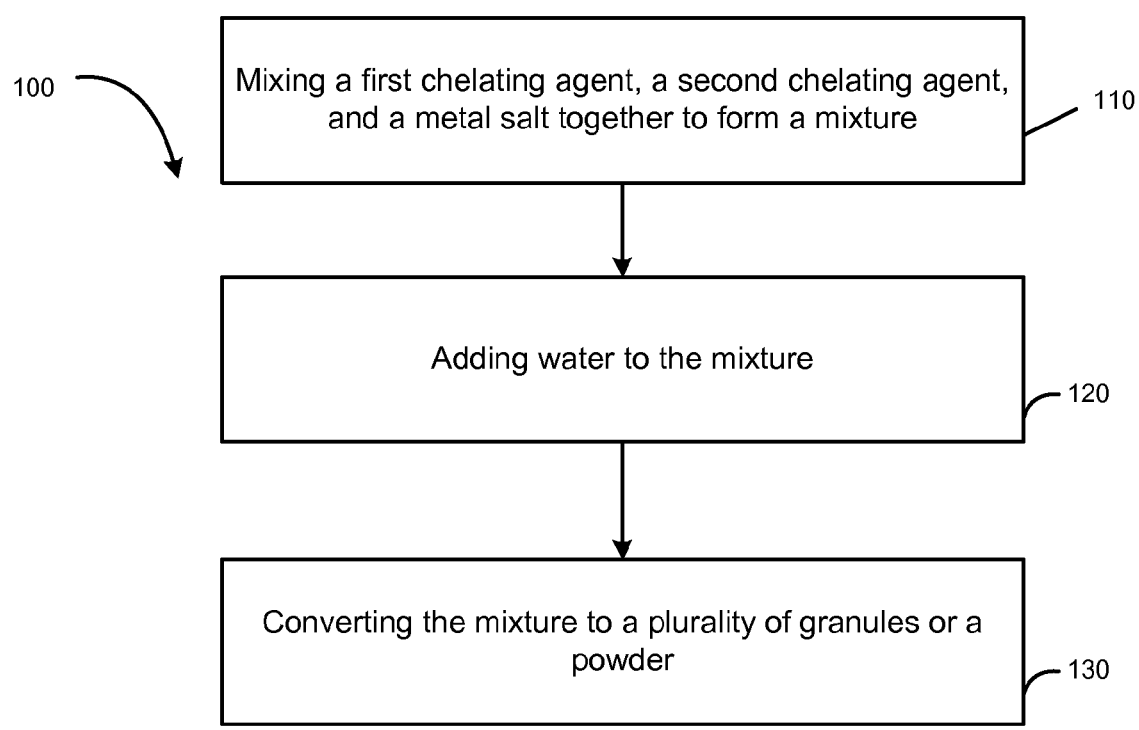

CHELATED COMPOSITIONS AND METHODS OF MAKING AND USING THE SAME

CROSS-REFERENCE TO RELATED APPLICATION

This application is a continuation application and claims the benefit of U.S. application Ser. No. 14/195,560, filed on Mar. 3, 2014 and titled "CHELATED COMPOSITIONS AND METHODS OF MAKING AND USING THE SAME", which is a continuation application and claims the benefit of U.S. application Ser. No. 12/976,627, filed on Dec. 22, 2010 and titled "CHELATED COMPOSITIONS AND METHODS OF MAKING AND USING THE SAME", now U.S. Pat. No. 8,685,133, each of which is incorporated herein by reference in entirety.

TECHNICAL FIELD

This disclosure relates generally to the manufacture and composition of chelated micronutrients for use in agriculture and animal husbandry. More particularly, this disclosure relates to a group of micronutrient metals bound in a network of chelator or chelating agent molecules.

BACKGROUND

Small amounts of iron, copper, manganese, cobalt, magnesium, calcium, and zinc have been determined to be helpful, if not necessary, for plant and animal life. In the course of agriculture, the soil or other growing medium can become depleted of these elements due to plant uptake, and other factors such as erosion, insolubility from combination with other materials in the soil, and/or weathering. Thus, there is a need to replenish these micronutrients so that the growing medium can be reused for new crops. A lack of or a depletion of these micronutrients can create a multitude of problems, including, but not limited to, stunted growth and crop loss. Additionally, livestock animals that feed on grasses and other vegetation that are low in micronutrients do not obtain their full requirement of micronutrients and thereby may suffer poor health and/or slow growth.

Micronutrient replenishment has been handled by the direct bulk addition of metal sulfates to the soil. This method had some drawbacks. First, the majority of the metal sulfate would either run off in the first water application, leach into lower levels of the soil, or the metal would oxidize and have limited bioavailability. Second, in neutral or alkaline soils, for example chalcareous soils, the metal ions would react and precipitate as insoluble, and non-bioavailable, oxides and hydroxides.

Chelates have been developed and provide a means to maintain bioavailability of the micronutrient metals by binding with the coordination sites of the metal ions to maintain their mobility and bioavailability. For example, ethylenediamine tetraacetic acid ("EDTA") can recruit up to six coordination sites in the form of four carboxylic acid moieties and two amine moieties, thereby forming a cage-like structure that resists any reactivity with oxide or hydroxide ions present in the metal ion's environment. Accordingly, the metal ion can retain its bioavailable state even in the presence of reactive caustic anions until it can contact a root hair and be taken up by the plant.

The manufacture of known metal chelates has traditionally included a process of dissolving a metal salt in a large amount of water, then adding the chelator, and then drying the reaction product until it crystallizes. This process is energy-, water-, and time-intensive.

Accordingly, it is desirable to provide a metal chelated product that creates a metal-chelator network and that may be manufactured by a process that minimizes the amount of water and subsequent drying needed. This manufacturing process can be adapted to produce either granulated chelated micronutrients, which are typically intended to remain in semi-solid form for a period of time in the soil, or micronutrient powders, which typically are intended to dissolve into water quickly and completely.

SUMMARY

A composition includes a first chelating agent, a second chelating agent, and a plurality of metal ions. In one embodiment, the second chelating agent includes citric acid and is different than the first chelating agent.

In some embodiments, the first chelating agent includes ethylenediamine tetraacetic acid. In other embodiments, the first chelating agent includes tetrasodium ethylenediamine tetraacetate.

In some embodiments, the first chelating agent includes a chelating molecule that has a moiety and the second chelating agent includes a chelating molecule that has a moiety. One of the plurality of metal ions has at least a first coordination site and a second coordination site. The first coordination site is occupied by the first moiety of the chelating molecule of the first chelating agent and the second coordination site is occupied by the first moiety of the chelating molecule of the second chelating agent.

In some embodiments, the first chelating agent includes a chelating molecule and the second chelating agent includes a chelating molecule. One of the plurality of metal ions is bound to the chelating molecule of the first chelating agent and to the chelating molecule of the second chelating agent.

In some embodiments, the first chelating agent includes a chelating molecule, and the second chelating agent includes a chelating molecule. The chelating molecule of the first chelating agent is bound to the chelating molecule of the second chelating agent.

In some embodiments, the composition includes a plurality of granules. In some embodiments, one of the plurality of granules includes at least one molecule of the first chelating agent, at least one molecule of the second chelating agent, and at least one of the plurality of metal ions.

In some embodiments, the composition is a water-soluble powder. In some embodiments, the powder has a plurality of particles. One of the plurality of particles includes at least one molecule of the first chelating agent, at least one molecule of the second chelating agent, and at least one of the plurality of metal ions.

In some embodiments the first chelating agent, the second chelating agent, and the plurality of metal ions form a network of chelated metal ions.

A method for forming a composition includes mixing a first chelating agent, a second chelating agent, and a metal salt together to form a mixture and processing the mixture to form at least one of a granulated composition and a powdered composition. In some embodiments, the second chelating agent includes citric acid and is different than the first chelating agent.

BRIEF DESCRIPTION OF THE DRAWINGS

The FIGURE is a flow chart illustrating a method of forming a chelated metal composition according to an embodiment of the invention.

DETAILED DESCRIPTION

This disclosure relates generally to the manufacture and composition of chelated micronutrients for use in agriculture and animal husbandry. More particularly, the disclosure relates to group of micronutrient metals bound in a network of chelator molecules. In some embodiments, the network of chelator molecules provides superior agronomic and metabolic efficacy as compared to traditional chelated micronutrient metals. In some embodiments, these micronutrients-in-network materials can be designed, for example, for longer term soil stability as solid-phase granules, or as powders for immediate and complete solubility and use as foliar applications or for ingestion by livestock. In some embodiments, the processes of making these micronutrients-in-network materials not only create the novel network structure, but also allow chelated micronutrients to be manufactured at significantly lower cost and effort than traditional chelated micronutrients.

Some chelates have a one-to-one ratio of chelated metal ion to chelator. For example, the EDTA is considered to bind to a single metal ion using the usual six coordination sites present in an octahedral structure available to period 4 transition metals. However, in some cases, one of the amine moieties does not become ionized until pH reaches above about 10. So, in some cases it is not necessary for all six coordination sites on a metal ion to be bound to a chelator for the metal to be considered chelated. Other chelators, such as citric acid and nitrilotriacetic acid ("NTA"), only have three or four chelation sites and so, they can never by themselves bind all six coordination sites of a single metal ion.

In some cases, metal ions are held in chelation and protected from precipitation when three or two coordination sites are occupied by chelator moieties. In some embodiments, it was found that metal ions can be maintained in chelation when two or three of the ion coordination sites are occupied by chelator moieties that do not necessarily belong to the same chelator molecule. The arrangement of chelator molecules joining across metal ion coordination sites creates a network of chelated metal that in some cases helps resist alkali disruption better than traditional chelates, is cheaper to manufacture, and/or still maintains the metal ion in the liquid and bioavailable state in high pH environments. For example, in some embodiments, the arrangement of chelator molecules maintains the metal ion in the liquid and bio-available state in environments that are above a pH of 9 or above a pH of 10.

In some embodiments, the use of multiple chelators or chelating agents, such as citric acid and EDTA (or its conjugate base) (each of which contain multiple moieties for bonding or association to coordination sites of a metal ion), can be induced to bond not only across a single metal ion, but also to bind to other chelator molecules, thereby creating a shared network of chelated metal ions in a random distribution of linked chelators. In some embodiments, the distribution of linked chelators is an ordered distribution.

In some embodiments, the manufacturing process that creates the metal-chelator network discussed above minimizes the amount of water and subsequent drying required by pre-existing methods. Furthermore, in some embodiments, the manufacturing process can be adapted to produce either granulated chelated micronutrients, which are typically intended to remain in semi-solid form for a period of time in the soil, or micronutrient powders, which typically are intended to dissolve into water quickly and completely. For example, in some embodiments, the powder dissolves into water within a few minutes (or even less than 30 seconds).

In some embodiments, a composition or a chelated micronutrient includes a network of chelators and metal ions which is capable of maintaining its micronutrient metal in solution above the pH where the oxide or hydroxide of the micronutrient metal would normally precipitate, and the means to manufacture such. The chelation network is formed by reacting a mixture of organic chelators concurrently with a metal salt, while simultaneously controlling the water content of the mixture to promote network formation. In some embodiments, the manufacturing process helps prevent the formation of separate metal-EDTA chelates and metal-citrate chelates in the end product.

In some embodiments, the intermixed network of chelated micronutrient allows the metal to be chelated in the most bioavailable valence state of the metal. For example, in one embodiment, iron is chelated as Fe(II), instead of the more usual Fe(III). This allows uptake and use by the target organism (such as a plant) without having to reduce the Fe(III), by metabolites or other biochemical means, to a valence state available to the metabolism of the organism. Additionally, in some embodiments, the composition, without any insoluble fillers, is 100% soluble, which is equal to the solubility of traditional metal-EDTA chelates.

In some embodiments, the intermixed network of chelated metal provides superior buffering against alkaline soil particles. For example, the chelated metal might come into contact with alkaline soil particles such as carbonates and/or hydroxides. Because the alkali in natural soils is not homogeneously distributed, but is in fact unevenly micro-distributed among the faces and interiors of assorted soil particles, metals, including non-buffered chelated metals, come into contact with micro-environments that can be significantly higher or lower in pH than the overall average pH of the bulk soil. Metal ions, including non-buffered metal chelates, that traverse the soil and come into contact with micro-pockets of alkaline pH higher than their precipitation point are precipitated within that micro-pocket of alkaline pH and are thereby rendered unavailable as a plant nutrient. In some embodiments, the composition provides a buffering action that resists contact with up to eight times the amount of alkaline materials before precipitating out of solution, as compared to traditional non-buffered chelates. For example, in some embodiments, a standard EDTA chelate might absorb one portion or mole of alkali before the pH rises and a precipitate forms while the buffering action of the composition of the present invention absorbs 8 portions or moles before its pH rises and a precipitate is formed.

In some embodiments, the method of production of the composition ensures that the complexation reactions are substantially completed, while at the same time the total water used is minimized or reduced.

Composition

In some embodiments, the composition includes a first chelating agent, a second chelating agent, and a plurality of metal ions. The first chelating agent is different than the second chelating agent. In other words, the first chelating agent has a different chemical make-up (i.e., has a different chemical formula) than the second chelating agent.

The first and the second chelating agents can be any type of chelating agent. For example, the first chelating agent and the second chelating agent can be any one of the following: disuccinic acid, nitrilo triacetic acid, glucoheptonate, monoethanolethylenediamine triacetic acid, diethanolethylenediaminediacetic acid, diethylenatriamine pentacetic acid, monoethanoldiethylenetriaminetetraacetic and (i.e., N-hydroxyethyl or N'-hydroxyethyl), diethanoldiethylenetriamine-triacetic acid (i.e., N,N'-dihydroxyethyl or N',N''-dihydroxethyl), and the corresponding compounds based upon propylene, isopropylene, methylethylene and cyclohexylene. In some embodiments, the first chelating agent is EDTA (or its conjugate base) and the second chelating agent is citric acid.

The metal ion can be an ion of any metal, including but not limited to iron, copper, manganese, cobalt, magnesium, calcium, and zinc. In some embodiments, the source of the metal ion is a metal salt. For example, in some embodiments, a metal salt such as a sulfate hydrate, a chlorine, or a nitrate, can be the source of the metal ion.

In some embodiments, the composition forms a network of chelated metal ions. Specifically, in some embodiments, a single metal ion is bound to a molecule of the first chelating agent and to a molecule of the second chelating agent. More specifically, in some embodiments, a single metal ion is directly bound to a molecule of the first chelating agent and is directly bound to a molecule of the second chelating agent. For example, a single metal ion may be bound at a first coordination site of the metal ion to a moiety of a molecule of the first chelating agent and may be bound at a second coordination site of the metal ion to a moiety of a molecule of the second chelating agent. In other embodiments, a single metal ion may be directly bound to a molecule of the first chelating agent and indirectly bound to a molecule of the second chelating agent. In other words, the metal ion is removed from direct bonding to the molecule of the second chelating agent but is indirectly bound to the molecule of the second chelating agent because both the metal ion and the molecule of the second chelating agent are bound in the same network.

Additionally, in some embodiments, the composition includes molecules of the first chelating agent that are directly bound to molecules of the second chelating agent.

In some embodiments, the composition includes a ratio of chelated metal ions to total chelator molecules that is greater than 1 to 1. For example, in some embodiments, the composition includes more chelated metal ions than total chelator molecules.

In some embodiments, additional materials are also added to the mixture. For example, in some embodiments, a filler such as ammonium sulfate or iron oxide fines are added to the mixture. In some embodiments, a granulation aid is added to the mixture. For example, in some embodiments, a granulation aid such as water, lignin sulfonate, or ethyl alcohol is added to the mixture.

In some embodiments, the composition is in the form of a plurality of granules. For example, in some embodiments, the granules of the composition have a diameter of about 0.25 inches (6.35 mm). In other embodiments, the granules have a diameter of less than 0.25 inches (6.35 mm). In yet further embodiments, the granules have a diameter of greater than 0.25 inches (6.35 mm). In some embodiments, one or each of the granules of the composition includes at least one molecule of the first chelating agent, at least one molecule of the second chelating agent, and at least one metal ion. For example, in some embodiments, one or each of the plurality of granules includes a network of chelated metal ions.

In some embodiments, the granules are solid and partially-soluble. In some embodiments, the granules are configured to retain the chelated metal in ionic form within the soil for a period of up to one year.

In other embodiments, the composition is in the form of a powder. Specifically, in some embodiments the composition is a powder that includes a plurality of particles. In some embodiments, the particles are between 1.18 mm and 0.6 mm in diameter. In some embodiments, the particles are greater than 1.18 mm in diameter. In yet further embodiments, the particles are less than 0.6 mm in diameter. In some embodiments, one or each of the particles of the powder of the composition includes at least one molecule of the first chelating agent, at least one molecule of the second chelating agent, and at least one metal ion. For example, in some embodiments, one or each of the particles includes a network of chelated metal ions. In some embodiments, the powder of the composition is partially-soluble. In other embodiments, the powder of the composition is completely soluble.

In some embodiments, the composition includes a coating. For example, in some embodiments, the composition includes a coating that is configured to control the release of the metal ions from the chelated network. In some embodiments, the coating is a polymer coating. In other embodiments, the coating is a wax coating. In some embodiments, the coating is formed of a biodegradable material.

For example, in some embodiments, the granules of the composition are covered or substantially covered with a coating.

Manufacture

The FIGURE is a flow chart that illustrates a method 100 of making the metal chelated composition. In some embodiments, an amount of a first chelating agent, an amount of a second chelating agent, and an amount of a metal salt are mixed together 110. In some embodiments, water is added to the mixture 120. Finally, in some embodiments, the mixture is converted or processed into a plurality of granules or a powder 130.

In some embodiments, an amount of a metal salt is added to the container for mixture. For example, in some embodiments, 200 to 1500 pounds (lbs.) of metal salt is used per ton of product desired. More specifically, in some embodiments, 480 to 1000 lbs. of metal salt is used per ton of product desired. In other embodiments, more or less of the metal salt is added to the container for mixture.

In some embodiments, the metal may be any transition metal, including iron, nickel, cobalt, zinc, copper, or manganese, or an alkaline earth metal, including magnesium or calcium. In one embodiment, the transition metal is iron, cobalt, zinc, copper, or manganese. In one embodiment, the metal is either magnesium or calcium. In one embodiment, the metal is a mixture of two or more transition metal salts or alkaline earth metal salts. In one embodiment the metal salt is a sulfate, a chloride, or a nitrate.

In some embodiments, a first chelating agent is added to the container for mixture. In some embodiments, the first chelating agent is either EDTA or $Na_4EDTA$. In some embodiments, 1 to 150 lbs. of EDTA solid or its conjugate base ("tetrasodium ethylenediamine tetraacetate" or "$Na_4EDTA$") in 39% aqueous solution per ton of product desired is added to the container for mixture. In one embodiment, the weight of the EDTA solid or $Na_4EDTA$ that is added is between 1% and 75% of the weight of the metal salt that is added.

In one embodiment, EDTA solid or acid is used to eventually create a granular final product. In another embodiment, $Na_4EDTA$ in 39% aqueous solution is used to create a powder final product. In other embodiments, a sodium or potassium salt of EDTA is used in dry powdered form to create either a granular or a powder final product.

For example, in some embodiments, tetrasodium ethylenediamine tetraacetate in a powder form is used in the composition.

In some embodiments, a second chelating agent is added to the container for mixture. For example, in some embodiments, 400 to 900 lbs. of citric acid per ton of product desired is added to the container for mixture. In some embodiments, the weight of the citric acid that is added is between 25% and 450% of the weight of the metal salt that is added. In some embodiments, trisodium citrate is used in place of citric acid.

In some embodiments, the metal salt, the first chelating agent, and the second chelating agent are mixed together. For example, they may be mixed in a mixing container using a known mixing method. In some embodiments, water is then added to the mixture to create a material with the consistency of wet sand (in other words, the mixture is not entirely saturated). In some embodiments, the weight of the water added is between 100 and 300 lbs. In some embodiments, the weight of the water added to the mixture (i.e., the mixture of the metal salt, the first chelating agent, and the second chelating agent) is less than 60% of the weight of the mixture. In some embodiments, the weight of the water added to the mixture is less than 30% of the weight of the mixture. In some embodiments, the weight of the water added to the mixture is less than 15% of the weight of the mixture.

In some embodiments, the citric acid is between 35% and 55% of the total weight of the mixture (citric acid, EDTA, and the metal salt), the EDTA is between 3% and 20% of the total weight of the mixture, and the metal salt is between 35% and 55% of the total weight of the mixture. For example in some embodiments, the citric acid is about 45% of the total weight, the EDTA is about 10% of the total weight, and the metal salt is about 45% of the total weight.

The wetted material is mixed for a period of time sufficient for the substitution reactions to begin with the metal ion coordination sphere, thereby creating the networked metal chelate. For example, in some embodiments, the wetted material is mixed by turning the material in a container or mixer.

The material is then processed to form the final product. In some embodiments, the final product is a granulated product. In other embodiments, the final product is a powdered product.

In some embodiments, the processing includes granulation, drying, and screening. Specifically, in some embodiments, the material is passed through a rotating granulation drum and additional water is added as needed to substantially complete the chelation reactions and to agglomerate the granules. In other embodiments, another granulation processed is used to agglomerate or form the granules.

Once the granules have been formed, the granules are dried. For example, in some one embodiment, the granules are passed through a gas-fired rotary drum dryer. In other embodiments, the granules are exposed to another drying process.

Once the granules have been dried, the granules are cooled. For example, in some embodiments, the granules are passed through a rotating drum cooler. In other embodiments, the granules are exposed to another cooling process.

The resulting material is then screened and collected. In some embodiments, the material is screened to a specific size, such as a +12/−4 screen size. In other embodiments, the material is screened to a larger or smaller size. In some embodiments, the particle size may range from −50 mesh for powders, and up to 0.25 inches in diameter for granules. In some embodiments, the oversized or larger materials are collected, ground, and screened again.

In some embodiments, 100 to 300 lb. of granulation aids are added to the existing mixture. Granulation aids include, but are not necessarily limited to: water, lignin sulfonate, and/or ethyl alcohol. All of these ingredients are then mixed to create the network of chelated metals and a sodium ionic salt. In one embodiment, this sodium ionic salt is sodium sulfate. In another embodiment, the sodium ionic salt is either sodium nitrate or sodium chloride.

In some embodiments, 1 to 1800 lbs. of filler material is added to the mixture to create a solid, partially-soluble, granule with a lower overall percentage (0.15 to 15%) of chelated metal that will continue to maintain ionic metal in the soil for up to one year. For example, in some embodiments, 1 to 400 lbs. of ammonium sulfate and/or 1 to 850 lbs. of iron oxide fines are added as filler. In some embodiments, to maximize the percentage of chelated metal, a filler is not added to the mixture.

Use

In some embodiments, the composition may be used in agriculture and/or livestock. For example, in some embodiments, the composition in the form of granules may be placed or disposed in or on soil that is proximate to a plant. For example, in some embodiments, the granules may be placed on or delivered to soil that a plant uses for nutrients. In some embodiments, such solid-phase granules can be designed for longer term soil stability.

In some embodiments, the composition in the form of a powder may be disposed in or on soil that is proximate to a plant. For example, the powder may be dissolved in a liquid such as water and then applied to the soil. In other embodiments, the powder may be dissolved in water and applied to the foliage of a plant or used for ingestion by livestock.

Example 1

Composition 850 lbs. of iron sulfate monohydrate was placed in a mixer with 750 lbs. of citric acid, 200 lbs. of ethylenediamine tetracetic acid and 100 lbs. of ammonium sulfate. These were thoroughly mixed and 200 lbs. of water was added. Although 200 lbs. of water was added in this embodiment, in other embodiments, more or less water was added. For example, in some embodiments, an amount of water equal to about 50% of the other materials is added. In other embodiments, an amount of water equal to about 30% of the weight of the other materials is added. The material was mixed for 15 minutes until it assumed the consistency of wet sand, then the material was conveyed to a rotating granulation drum. The material was rolled in the granulation drum with water added as necessary to agglomerate the material into granules or balls with an average diameter of 3 to 5 mm. The material was passed to a gas-fired rotary drier, then to a rotary cooler, and then screened to a +12/−4 mesh size.

Analysis

The finished material was tested by diluting it into fertilizer, then extracting it into an acetate/acetic acid buffer, then oxidizing all the available iron, then raising the pH above the precipitation point of aqueous Fe (III). The resulting liquid was then tested for iron content.

First, the material was ground in an analytical laboratory grinder. Additionally, standard 10-10-10 fertilizer (Vigoro) was ground by the same method. The iron chelate was diluted 20:1 by mixing 0.2556 g of chelate with 4.7827 g of 10-10-10 fertilizer. 1.2537 g of this mixture was weighed out and put into a 250 mL volumetric flask with 125 mL of an extraction buffer composed of: 1 g of sodium acetate and 25 mL of glacial acetic acid in a 1 L volumetric flask that was then filled with deionized water. 10 mL of household bleach (6% NaOCl) was added to the 250 mL volumetric flask to oxidize all the iron. Then 20 mL of a solution composed of 10 g of diammonium phosphate in 1 L deionized water was added to the 250 mL volumetric flask to raise the pH. The volumetric was then filled to volume with deionized water and 3 1.00 mL aliquot were removed. The aliquots were each diluted to a dilution factor of 16 and the samples were tested by atomic absorption spectroscopy. The aliquots were found to contain 14.4% chelated iron.

Example 2

Composition 480 lbs. of iron sulfate monohydrate were mixed with 300 lbs. of citric acid, 180 lbs. of ethylenediamine tetracetic acid, 100 lbs. of ammonium sulfate, and 820 lbs. of iron oxide fines. 200 lbs. of water were added while mixing to create a wet sand. The material was mixed for 15 minutes until it assumed the consistency of wet sand, then the material was conveyed to a rotating granulation drum. The material was rolled in the granulation drum with water added as necessary to agglomerate the material into granules or balls with an average diameter of 3 to 5 mm. The material was passed to a gas-fired rotary drier, then to a rotary cooler, and then screened to a +12/−4 mesh size.

Analysis

The finished material was tested by diluting it into fertilizer, then extracting it into an acetate/acetic acid buffer, then oxidizing all the available iron, then raising the pH above the precipitation point of aqueous Fe(III). The resulting liquid was then tested for iron content.

First, the material was ground in an analytical laboratory grinder. Additionally, standard 10-10-10 fertilizer (Vigoro) was ground by the same method. The iron chelate was diluted 20:1 by mixing 0.2549 g of chelate with 4.7646 g of 10-10-10 fertilizer. 1.2493 g of this mixture was weighed out and put into a 250 mL volumetric flask with 125 mL of an extraction buffer composed of: 1 g of sodium acetate and 25 mL of glacial acetic acid in a 1 L volumetric flask that was then filled with deionized water. 10 mL of household bleach (6% NaOCl) was added to the 250 mL volumetric flask to oxidize all the iron. Then 20 mL of a solution composed of 10 g of diammonium phosphate in 1 L deionized water was added to the 250 mL volumetric flask to raise the pH. The volumetric was then filled to volume with deionized water and 3 1.00 mL aliquot were removed. The aliquots were each diluted to a dilution factor of 16 and the samples were tested by atomic absorption spectroscopy. The aliquots were found to contain 5.02% chelated iron.

Example 3

Composition 1000 lbs. of zinc sulfate was mixed with 700 lbs. of citric acid and 300 lbs. of 39% aqueous tetrasodium ethylenediamine tetraacetate. The material was mixed until it reached the consistency of wet sand, then the material was conveyed to a rotating granulation drum. The material was rolled in the granulation drum for about 20 minutes to allow the chelation reactions to complete. The material was passed to a gas-fired rotary drier, then to a rotary cooler, and then screened to a −30 mesh size.

Analysis

The finished material was tested by titration with 0.5 M NaOH. A 1% w/w solution was made of the material by placing 1.0042 g in a 100 mL of deionized water. 0.5 M NaOH was then titrated into this solution. The material absorbed 23.8 mL of the 0.5 M NaOH while the solution pH rose from about 2 to about 10.2, whereupon a precipitate formed. In contrast, pure zinc EDTA chelate was found to absorb 5.8 mL of the NaOH solution until its pH went above 10.2 and a precipitate formed.

Example 4

Composition 1100 lbs. of calcium chloride was mixed with 900 lbs. of citric acid and 2.2 lbs. of powdered tetrasodium ethylenediamine tetraacetate. This dry material was passed to a rotating granulation drum wherein water was added to bring the material to the consistency of damp powder. After 40 minutes, the material was passed to a gas-fired rotary drier, then to a rotary cooler, and then screened to a −30 mesh size.

Analysis

Samples were dissolved in water and tested by atomic absorption spectroscopy, which showed a 17.8% calcium content.

Example 5

Analysis 20.0090 g of iron sulfate monohydrate was placed in a 1.000 volumetric flask with about 800 mL of deionized water. The mixture was shaken for 20 minutes, then 9.0034 g of citric acid and 1.0012 g of tetrasodium ethylenediamine tetraacetate were added and the flask was filled to volume with deionized water. The flask was shaken for 25 minutes, during which time the solution turned a clear yellow color.

1.00 mL of the yellow solution was added to a 250.00 mL volumetric flask with 125 mL of an extraction buffer composed of: 1.00 g of sodium acetate and 25.0 mL of glacial acetic acid in a 1.000 L volumetric flask that was then filled with deionized water. 10.00 mL of household bleach (6% NaOCl) was added to the 250.00 mL volumetric flask to oxidize all the iron. Then 25.00 mL of a solution composed of 10.00 g of diammonium phosphate in 1.000 L deionized water was added to the 250.00 mL volumetric flask to raise the pH. The 250.00 mL volumetric was then filled to volume with deionized water and shaken. The resulting solution was filtered, then tested for iron content on by an atomic absorption spectrophotometer (Buck Scientific 200A) at 248.3 nm.

Total theoretical iron present in the aliquot was 6.58 ppm and total iron found was 5.26 ppm. This was 79.95% of the total theoretical iron and corresponds to a molar ratio of chelators per iron of 0.52. Differently stated, the atomic absorption spectrophotometer revealed a molar ratio of 1.92 iron(III) ions per chelator molecule (a ratio greater than one chelated metal ion per chelator molecule) being maintained in its liquid state at a pH above the normal precipitation point of non-chelated iron (III).

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the embodiments.

What is claimed is:

1. A method of providing nutrients to an animal, comprising:
    delivering a composition to the animal, the composition including a first chelating agent, a second chelating agent different than the first chelating agent and an ion,
    wherein the first chelating agent includes at least one selected from the group consisting of ethylenediamine tetraacetic acid and tetrasodium ethylenediamine tetraacetate and the second chelating agent includes citric acid, wherein the composition forms a network of chelated ions, and wherein the composition is in the form of at least one of the group consisting of a plurality of granules and a water-soluble powder.

2. The method of claim 1, wherein the composition is in the form of a plurality of granules.

3. The method of claim 1, wherein the composition is in the form of a plurality of granules, one of the plurality of granules includes at least one molecule of the first chelating agent, at least one molecule of the second chelating agent, and at least one of the plurality of metal ions.

4. The method of claim 1, wherein the composition is in the form of a water-soluble powder.

5. The method of claim 1, wherein the composition is a water-soluble powder, the powder having a plurality of particles, one of the plurality of particles includes at least one molecule of the first chelating agent, at least one molecule of the second chelating agent, and at least one of the plurality of metal ions.

6. The method of claim 1, wherein the composition is in the form of a water-soluble powder, the method further comprising dissolving the composition in an aqueous solution prior to the delivering.

7. A method of providing nutrients to an animal, comprising:
    delivering a composition to the animal, the composition including a first chelating agent, a second chelating agent different than the first chelating agent and an ion,
    wherein the first chelating agent includes at least one selected from the group consisting of ethylenediamine tetraacetic acid and tetrasodium ethylenediamine tetraacetate and the second chelating agent includes citric acid.

8. The method of claim 7, wherein the composition is in the form of a plurality of granules.

9. The method of claim 7, wherein the composition is in the form of a plurality of granules, one of the plurality of granules includes at least one molecule of the first chelating agent, at least one molecule of the second chelating agent, and at least one of the plurality of metal ions.

10. The method of claim 7, wherein the composition is in the form of a water-soluble powder.

11. The method of claim 7, wherein the composition is a water-soluble powder, the powder having a plurality of particles, one of the plurality of particles includes at least one molecule of the first chelating agent, at least one molecule of the second chelating agent, and at least one of the plurality of metal ions.

12. The method of claim 7, wherein the composition is in the form of a water-soluble powder, the method further comprising dissolving the composition in an aqueous solution prior to the delivering.

* * * * *